United States Patent [19]

Osten et al.

[11] Patent Number: 5,719,950
[45] Date of Patent: Feb. 17, 1998

[54] BIOMETRIC, PERSONAL AUTHENTICATION SYSTEM

[75] Inventors: David W. Osten, Grant Township, Washington County; Hatim M. Carim, West St. Paul, both of Minn.; Michael R. Arneson, Westminister, Md.; Bradford L. Blan, Cropwell, Ala.

[73] Assignee: Minnesota Mining and Manufacturing Company, St. Paul, Minn.

[21] Appl. No.: 513,741

[22] Filed: Aug. 30, 1995

Related U.S. Application Data

[63] Continuation of Ser. No. 217,433, Mar. 24, 1994, abandoned.
[51] Int. Cl.$^6$ ................................................. G06K 9/00
[52] U.S. Cl. ................................... 382/115; 340/825.54
[58] Field of Search ............................... 382/115, 117, 382/118, 126; 128/640; 340/825.34, 825.31, 825.54, 573

[56] References Cited

U.S. PATENT DOCUMENTS

| | | | |
|---|---|---|---|
| 4,449,189 | 5/1984 | Feix et al. | 364/513.5 |
| 4,524,087 | 6/1985 | Engel | 427/2 |
| 4,539,996 | 9/1985 | Engel | 128/640 |
| 4,554,924 | 11/1985 | Engel | 128/640 |
| 4,641,349 | 2/1987 | Flom et al. | 382/2 |
| 4,671,298 | 6/1987 | Babb et al. | 128/719 |
| 4,749,553 | 6/1988 | Lopez et al. | 128/719 |
| 4,848,353 | 7/1989 | Engel | 128/640 |
| 4,857,916 | 8/1989 | Bellin | 382/2 |
| 4,869,254 | 9/1989 | Stone | 128/633 |
| 4,896,363 | 1/1990 | Taylor | 382/5 |

(List continued on next page.)

FOREIGN PATENT DOCUMENTS

| | | | |
|---|---|---|---|
| 0 082 304 | 6/1983 | European Pat. Off. | A61B 5/00 |
| 0 121 222 | 10/1984 | European Pat. Off. | G07C 9/00 |
| 0 308 162 | 3/1989 | European Pat. Off. | A61B 5/10 |
| 3731773 C1 | 6/1983 | Germany | G07C 9/00 |
| 3834048 A1 | 4/1990 | Germany | G07C 9/00 |
| 8503290 | 6/1987 | Netherlands | G07C 9/00 |
| WO 90/08366 | 7/1990 | WIPO | G07C 9/00 |

OTHER PUBLICATIONS

Portions of *Thumb Scan Proposal;* 3M; St. Paul, Minnesota; Jun. 1988.
Portions of *A Proposal to: Ford Aerospace Corporation;* 3M; St. Paul, Minnesota; Feb. 1990.
*A Rough Order of Magnitude;* 3M; St. Paul, Minnesota; Nov. 1991; pp. 1–9.
Scott, Walter R., *Fingerprint Mechanics, A Handbook; Fingerprints from Crime Scene to Courtroom,* 1st Ed. Springfield, Ill., Thomas (c1951), XXII, pp. 7–27.
Letter to Mike Arneson from Ries Robinson dated Feb. 8, 1993.
*Webster's Third New International Dictionary,* vol. II H to R; Encyclopedia Britannica, Inc., Chicago, Illinois; 1986; p. 1767.
Identix Incorporated, Identix TouchLock™Physical Access Control Brochure (May 1993).
Identix Incorporated, Identix TouchLock™Data Access Control Brochure (May, 1993).
Identix Incorporated, Identix TouchPrint™Brochure (Feb. 1993).

*Primary Examiner*—Yon J. Couso
*Attorney, Agent, or Firm*—Gary L. Griswold; Walter N. Kirn; John H. Hornickel

[57] ABSTRACT

A personal, biometric authentication system is disclosed. The system can be used for controlling access to equipment or physical facilities. The system employs the combination of a unique, inherently specific biometric parameter recognized and compared with stored data and at least one non-specific biometric parameter of a physiological characteristic recognized and compared with physiological norms. Positive comparison results in authentication of an individual that is not incapacitated, dismembered, or deceased.

13 Claims, 10 Drawing Sheets

U.S. PATENT DOCUMENTS

| | | | |
|---|---|---|---|
| 4,952,928 | 8/1990 | Carroll et al. | 340/825.54 |
| 4,975,581 | 12/1990 | Robinson et al. | 250/339 |
| 4,993,068 | 2/1991 | Plosenka | 382/2 |
| 5,012,810 | 5/1991 | Strand | 128/640 |
| 5,067,162 | 11/1991 | Driscoll, Jr. et al. | 382/5 |
| 5,078,136 | 1/1992 | Stone | 128/633 |
| 5,103,486 | 4/1992 | Grippi | 582/4 |
| 5,133,356 | 7/1992 | Bryan et al. | 128/640 |
| 5,163,094 | 11/1992 | Prokoski | 382/2 |
| 5,202,929 | 4/1993 | Lemelson | 382/2 |
| 5,204,670 | 4/1993 | Stinton | 340/825.54 |
| 5,229,764 | 7/1993 | Matchett | 382/2 |
| 5,291,560 | 3/1994 | Daugman | 382/2 |

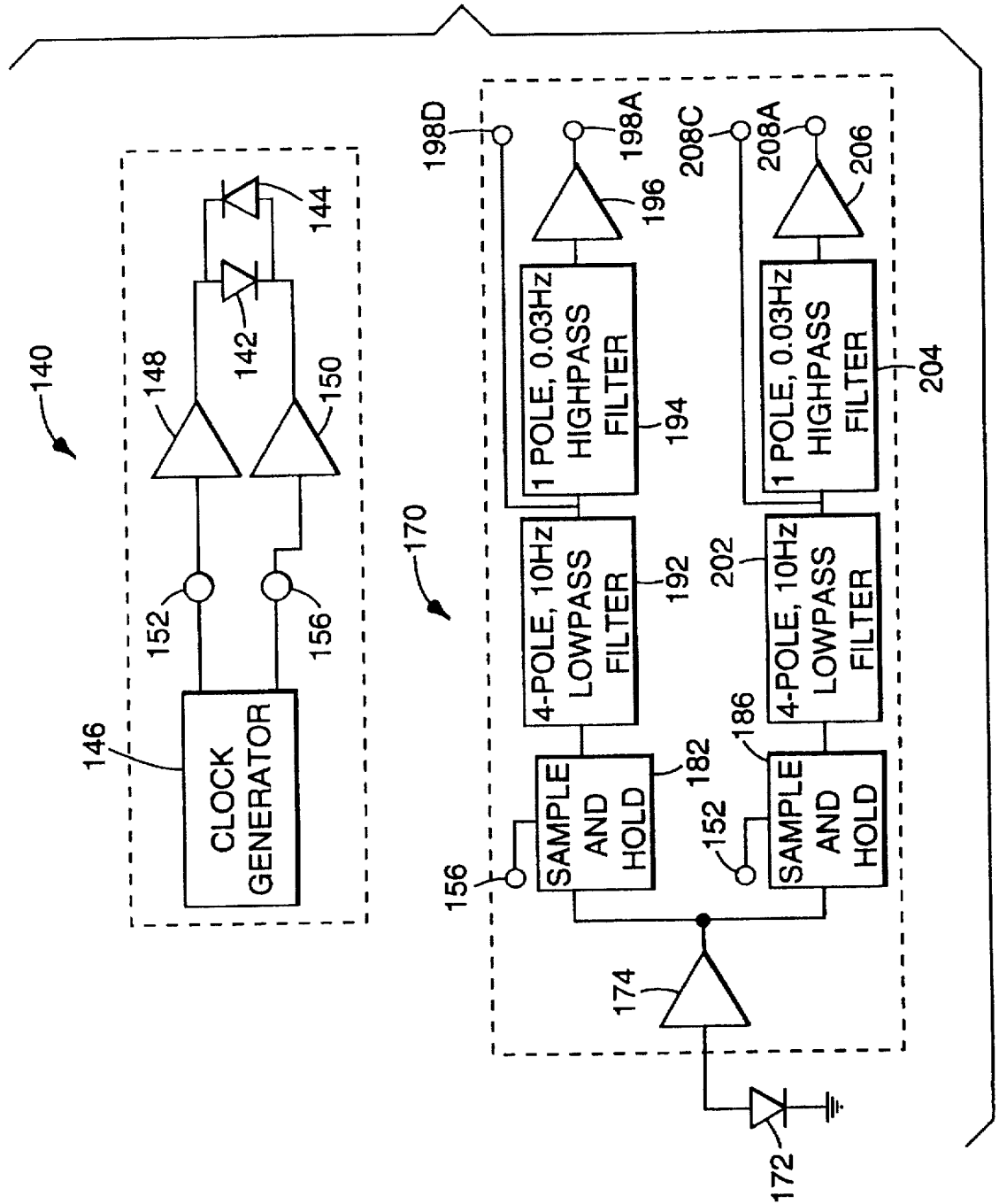

BIOMETRIC, PERSONAL AUTHENTICATION SYSTEM

This is a continuation of application Ser. No. 08/217,433 filed Mar. 24, 1994, now abandoned.

GOVERNMENT RIGHTS

This invention was made with Government support under Loral Subcontract SO-124465-S and MDA904-93-C4074. The Government has certain rights in this invention.

FIELD OF THE INVENTION

This invention relates to biometric, personal authentication systems that authenticate identities of individuals.

BACKGROUND OF THE INVENTION

Personal recognition systems generally utilize a single highly specific characteristic for identifying valid access requests, sometimes in association with another method of individual authentication.

Published patent application NL 8503290, (Sibum) according to an uncertified English translation teaches identifying a person by recognition of a stored pattern, e.g. fingerprint, preventing unauthorized access or use, using pattern analysis with determination of body heat and/or hair size and color to prevent use of a falsified replica of the fingerprint.

Published PCT patent application WO 90/08366 (Clayden) teaches identification of a person by monitoring one or a number of "biometric" parameters such as bone structure, temperature, fingernail pattern, creases in the palm or fingers of the hand and comparing the monitored data with stored characteristics. Further, teachings include reference to speech, handwriting and piano keyboard "signatures".

U.S. Pat. No. 4,896,363, (Taylor) teaches a method for analysis and comparison of a "live" fingerprint to a stored record and an apparatus for functional use of the method. Commercial products described in Taylor include personal access apparatus manufactured by Thumbscan Corporation.

U.S. Pat. Nos. 4,869,254 and 5,078,136 (both Stone et al.) teach a method for non-invasive measurement and calculation of oxygen saturation on blood in the human body under transient conditions and describe apparatus for functional use of the method. Commercial products described in Stone et al. are widely identified as pulse oximeters.

U.S. Pat. No. 5,103,486 (Grippi) teaches a scanning of a combination of fingerprint with an overwritten projection of a signature to identify an individual, and claims the projection of "any biological feature of the user". A biological feature is described as live skin tissue.

SUMMARY OF THE INVENTION

None of the authentication, recognition, or access control systems in the art recognize the problem that biometric devices can be circumvented by presenting the biometric pattern of an authorized individual seeking biometric, personal authentication who has been incapacitated, dismembered, or is deceased at the time of attempted authentication, recognition, or access.

Stated another way, none of the authentication, recognition, or access control systems in the art recognize the possibility that biometric parameters can be correlated or otherwise interrelated in order to assure that an individual seeking biometric, personal authentication is actually present for authentication. Existing devices can be circumvented by someone, other than the genuine person seeking authentication, actually presenting the biometric pattern of an authorized individual seeking biometric, personal authentication.

For example, a fingerprint analysis that does not recognize whether the finger is attached to a living human being can be circumvented by electronic or photographic reconstructions of the fingerprint or dismemberment of the finger. Other evidence the art presently employs for confirmation can be circumvented by use of subterfuge and substitution.

The present invention solves a problem unrecognized in the art by providing a biometric, personal authentication system that requires correlation among a unique, inherently specific biometric parameter with at least one non-specific biometric parameter in a physiologically acceptable range.

Previously, the art has considered two kinds of errors. The first kind is where the authentication system would erroneously reject authentication of a truly authorized user. The second kind of error is where the authentication system would erroneously accept authentication of a truly unauthorized user. Both kinds of error are based on the accuracy and precision of authentication based on a unique, inherently specific biometric parameter. The parameter can be too severely applied, (rejecting authentication when it should be accepted,) or too loosely applied, (accepting authentication when it should be rejected). In general, the two kinds of errors for a recognition system using a single, unique, inherently specific biometric parameter are inversely related. Reducing the error rate for false rejection increases the false acceptance rate, and vice versa. Authentication systems, especially access systems, are faced with this dilemma.

The present invention considers a third kind of error and solves a problem that the art has not recognized. An unrecognized third possible error is where the authentication system would erroneously accept authentication of a truly unauthorized user attempting to gain access using the pattern of a unique, inherently specific biometric parameter from an authorized user. The errors of the first and second kind, and solutions to treat such errors, do not consider or adequately measure the risk of circumvention of the authentication system.

The present invention solves errors of the third kind by providing an authentication system that recognizes a unique, inherently specific biometric parameter and other non-specific biometric parameters that need not be unique to the individual but are comparable to physiological norms and are variable during the time of authentication.

The present invention solves the problem that at least two modes of biometric recognition must fail or be circumvented in order to authenticate an unauthorized user.

"Biometric parameters" means dimensional and physiological characteristics of an individual human. Some biometric parameters (e.g., fingerprints (including thumbprints), palm prints, pore prints, voice prints, handwriting (including signature), and retinal configurations), are both unique and inherently specific and are relatively easy to copy and reproduce or model for later comparison for purposes of authentication. Fingerprint analysis refers to the identification and measurement of minutia points (bifurcations and end points). Pore print analysis refers to the identification and measurement of pores within the ridges of the fingers.

Other biometric parameters are non-specific and not unique to an individual. Some non-specific biometric parameters include dimensional characteristics (e.g., bone structure, and physical dimensions) and skin temperature that are not likely to have some variability during the time required for authentication and physiological characteristics (e.g., electrocardiographic (EKG) signals, pulse, and spectral characteristics of human tissue) that are likely to have some measurable variability during the time required for authentication. Of the two, physiological characteristics are more meaningful to biometric, personal authentication because such physiological characteristics are more difficult to simulate because such measurements are observable within physiological ranges, variable in time and, in characteristics such as EKG and pulse, synchronizable within a single human body.

One or more non-specific biometric parameters used in combination with one or more unique, inherently specific biometric parameters provides extremely high precision protection against circumvention, and does not require time consuming and inordinate measurement for authentication for purposes such as access control to a secure function or fitness to perform a function. Further non-specific physiological characteristics such as blood alcohol content or levels of controlled chemical substances (e.g., legal drugs used in illegal quantities or at illegal times or illegal drugs) in the body could be used to determine if an otherwise authorized user is authenticated to be in acceptable physical condition to be granted access to a motor vehicle or other facility or equipment.

The biometric, personal authentication system of the present invention comprises:

(a) storage subsystem to store a unique, inherently specific biometric parameter from at least one individual in a species;

(b) first recognition subsystem to detect the unique, inherently specific biometric parameter in an individual seeking personal authentication;

(c) second recognition subsystem to detect at least one non-specific biometric parameter of a physiological characteristic having measurable variability during the time of authentication in the individual seeking personal authentication;

(d) first comparison subsystem to compare the unique, inherently specific biometric parameter detected by the first recognition subsystem with the unique, inherently specific biometric parameter stored in the storage subsystem;

(e) second comparison subsystem to compare each non-specific biometric parameter to physiological norms for the species within an acceptable range; and (f) authentication subsystem to confirm identity of the individual seeking personal authentication by evaluating the comparisons made by first comparison subsystem and second comparison subsystem.

Desirably, an optional step (g) includes a subsystem to use successful authentication to provide access.

Preferably, the second recognition subsystem detects at least two non-specific biometric parameters with physiological correlation of the non-specific biometric parameters within an acceptable range. More preferably, the detection of at least two non-specific biometric parameters are synchronized. Examples of non-specific biometric parameters of physiological characteristics include bloodflow, spectral identity of tissue, electrocardiographic signals, pulse, blood oxygenation, hematocrit, biochemical assays of tissue, electrical plethysmography, skin exudates, mechanical properties of skin, electrical properties of skin, transpiration of gases, blood pressure, and differential blood volume.

Most preferably, the biometric, personal authentication system of the present invention utilizes fingerprint analysis (used in this invention to include thumbprint analysis) of an individual in combination with pulse oximetry and electrocardiography of the individual. The fingerprint analysis supplies the unique, inherently specific biometric parameter while the data from a pulse oximeter and EKG supplies the non-specific parameter(s), preferably both synchronized in time between two non-specific parameters and correlated between the non-specific parameters and the unique, inherently specific biometric parameter. Specifically the EKG signal as measured in real time is synchronized with the pulse measured by the pulse oximeter as change of rate of blood flow in real time.

For example, if the fingerprint analysis matches the unique, inherently specific biometric parameter, and if the pulse oximeter data of pulse and percentage oxygen saturation and EKG as non-specific biometric parameters correlate within acceptable norms, and if pulse is determined by two different and synchronizable methods (electrical and optical) to be synchronized, then the individual identified with the fingerprint is not incapacitated, dismembered, or deceased, and then authentication of the individual is achieved. Optionally, skin temperature can be added to provide further confirmation of viability of the individual seeking authentication.

With authentication of an individual according to the present invention, a variety of actions can be taken. Non-limited examples of actions available to the authenticated individual include access to equipment, access to physical facilities, recognition of the individual for a variety of reasons, confirmation of presence of the individual in an authorized location or using authorized equipment, and other situations where the status of an individual is remotely determined or controlled.

Beyond the first level of authentication of an individual and authorization of entry to a physical facility or use of equipment, suitability of performance may be verified for a second level of access control through measurement of blood gases or other characteristics, such as blood alcohol or controlled chemical substances levels, that would impair the individual's operation of equipment such as a mass transit vehicle.

A feature of the present invention is that inherently specific and non-specific biometric parameters can be concurrently and non-invasively gathered for recognition, comparison, and determination of authentication.

Another feature of the present invention is that non-specific biometric parameters need not be identified to the individual seeking personal identification.

An advantage of the present invention is that individuals seeking personal authentication undergo multiple biometric parameter comparison with security measures that potentially avoid false authentication.

One optional feature of the invention includes the use of information input and data entry apparatus to minimize searching of stored data of the unique, inherently specific biometric parameter, such as by use of a personal identification number or code, a photo, or other means.

Another optional feature of the invention includes apparatus for reading and analyzing encoded and encrypted information resident on magnetic or optical media or a hologram stored on a plastic card possessed by the individual seeking authentication, rather than stored in the apparatus for receiving data of the unique, inherently specific biometric parameter.

Another optional feature of the invention is to provide additional authentication using apparatus that identifies and compares more than one unique, inherently specific biometric parameters such as written signature, retinal configuration, voice recognition, or physical dimensions of the individual or features of the individual.

BRIEF DESCRIPTION OF THE DRAWINGS

FIG. 5 is a block diagram of the apparatus for recognizing the non-specific biometric parameter of blood oxygen saturation.

EMBODIMENTS OF THE INVENTION

Figure 1:
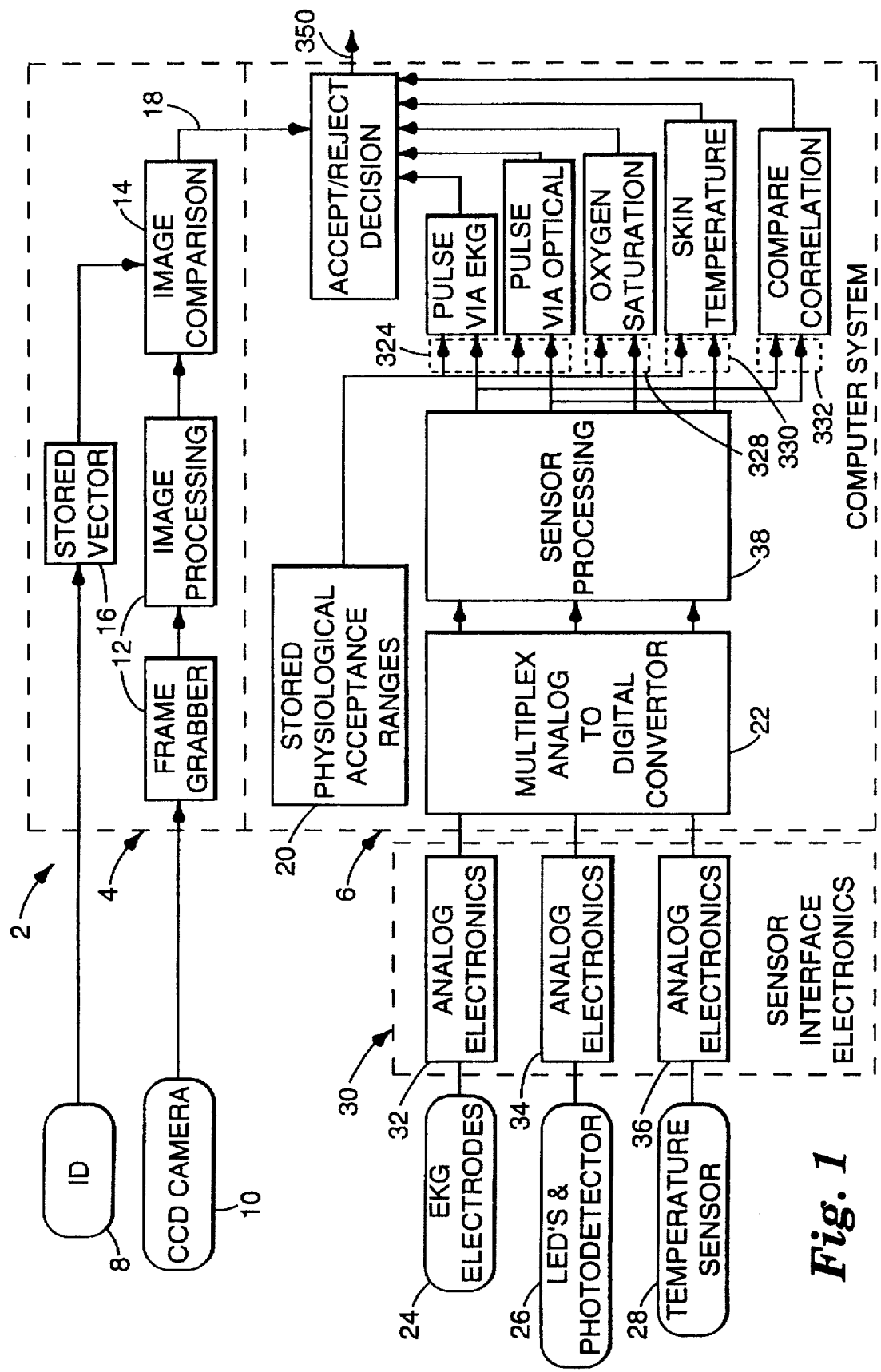
FIG. 1 is a schematic illustration of a preferred embodiment of the invention.

FIG. 1 shows a schematic of a preferred embodiment of the personal, biometric authentication system of the present invention. This embodiment is a counter top mounted access control unit containing the data entry and sensor apparatus. The access control is interconnected with a protected electronic computer system to provide authentication of the individual requesting entry and use of the system.

This embodiment utilizes a portion of the general purpose computer 2 for processing 6 of the non-specific biometric indicator data and processing 4 of the unique fingerprint image.

An individual seeking access first enters a identification code followed by placing both hands on contoured surfaces containing various sensors for a period of approximately ten seconds until authentication is completed successfully or unsuccessfully, and, preferably, access is granted or denied. Identification code entry 8 is a personal identification code number (PIN) or can be an identification card inserted and read to request access through the access system. Use of personal identification codes narrows the search process needed to compare the unique, inherently specific biometric parameter detected by the device with stored data. This acts to speed operations needed for establishing personal authentication. Further the PIN number can provide an additional, preliminary level of comparison in the authentication process.

Authentication system elements include fingerprint image sensor 10 inputing data for analysis to computer logic and memory functions 4 for unique, inherently specific identification, and non-specific biometric sensors 24, 26, and 28 with signal process functions 30 inputing information for analysis to computer system 6 to recognize electrocardiogram (EKG), pulse, and blood oxygen saturation for non-specific biometric validation and skin temperature for further optional validation. With this combination of information the individual seeking authentication and access can be uniquely identified and a determination can be made that the individual seeking authentication is not incapacitated, dismembered, or deceased. In other words, the biological state of the individual, as measured non-invasively via physiological characteristics that vary in time during the authentication, is used with the unique, inherently specific parameter of a fingerprint to authenticate that the individual is alive and functioning with acceptable physiological conditions for authentication and resulting access.

Fingerprint recognition camera 10 and system 4 employs well known apparatus, circuitry, and software. The individual's fingerprint pattern is detected by camera 10 when the individual places a thumb on detector window 42, (shown on FIG. 2 and described below). The detected image is captured and analyzed by image processor 12, developed into a vector array of fingerprint minutiae which is validated by comparator 14 through correlation of the scanned image vector array with the array selected from pre-stored memory file 16 indexed by PIN. If the image matches the stored information, then output 18 of comparator 14, is turned on, signaling the decision process as diagrammed in FIG. 7 and described below.

Fingerprint recognition systems such as camera 10 working with system 4 are commercially available from ThumbScan, Inc., Lombard Ill. Such system 4 is described in U.S. Pat. No. 4,896,363 (Taylor), the disclosure of which is incorporated by reference herein. Alternatively, camera 10 is commercially available as Model FC-11 Fingerprint Capture Station, from Digital Biometrics, of Minnetonka Minn. When Digital Biometrics camera 10 is used, then frame grabber IP-8 Image Processing Board commercially available from Matrox Electronic Systems, LTD, of Dorual, Quebec, Canada is also used, along with comparison software commercially available from BlitzMatch, Inc. of Champaign, Ill.

The pre-stored fingerprint selection pattern may be stored in a dedicated ROM memory of the fingerprint recognition system 4; or stored in the memory of computer terminal accessed by the individual through a standard key pad connected to a asynchronous I/O port; or entered into the security access system via a magnetic or optical identification card presented to the access instrument at the time of actuating the access system. The identification card may replace or supplement the entry of the PIN using the key pad.

Non-specific biometric recognition circuitry shown in FIG. 1 include biomedical (EKG) electrodes 24 communicating with analog signal processor 32, light emitting diode (LED) sources (one in the visible range (about 660 nm) and the other in the near infrared (NIR) range (about 910 nm)) and detector 26 communicating with timed power source and signal processor 34, for the plethysmographic signals of the blood pulse/oxygen monitor and temperature sensor 28 communicating with signal processor and ambient temperature sensor 36.

After analog processing, the signals are communicated to computer system 6 digitized for analysis through interface 22 (such as a RTI-815 card available from Analog Devices of Norwood, Mass. The digitized signals are processed within a general purpose computer CPU, for example a IBM PS/2, available from IBM Corporation of Armonk, N.Y. The sensor processing 38 follows a logic pattern programmable by a person of ordinary skill in programming the general computer of choice. The logic pattern includes a variety of calculating, smoothing and comparing steps as shown in the flow diagram of FIG. 7. Acceptances ranges are stored in memory 20 and compared with the individual data at decision states 324, 328, 330 and 332 as further defined within the flow diagram of FIG. 7.

Figure 2A:
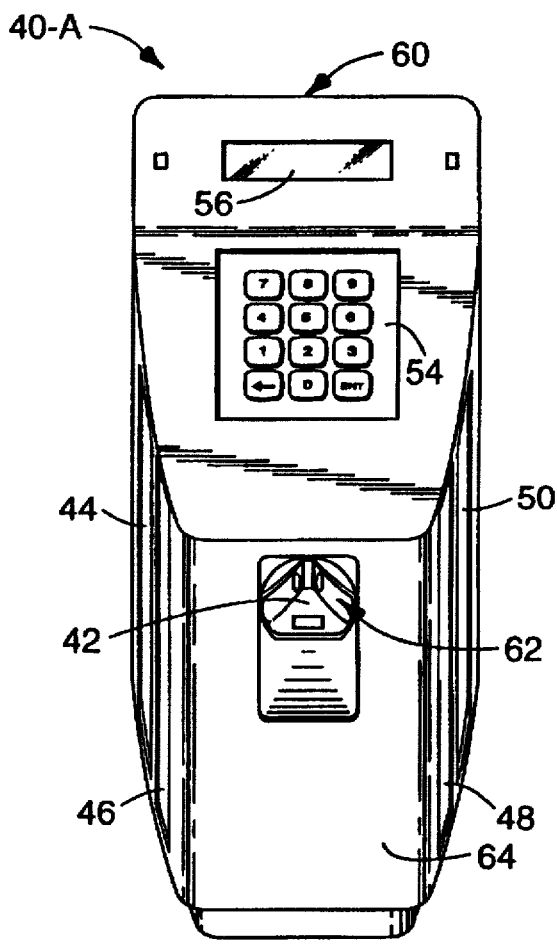
FIGS. 2a, 2b, and 2c are plan views of a preferred embodiment of the invention.
Figure 2C:
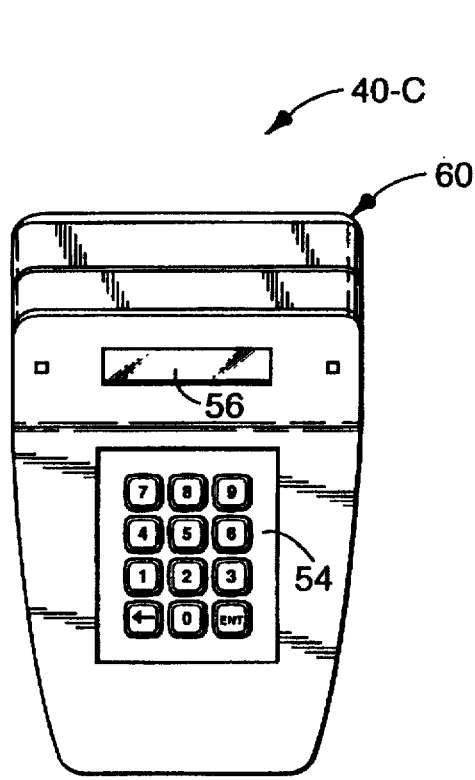
Figure 2B:
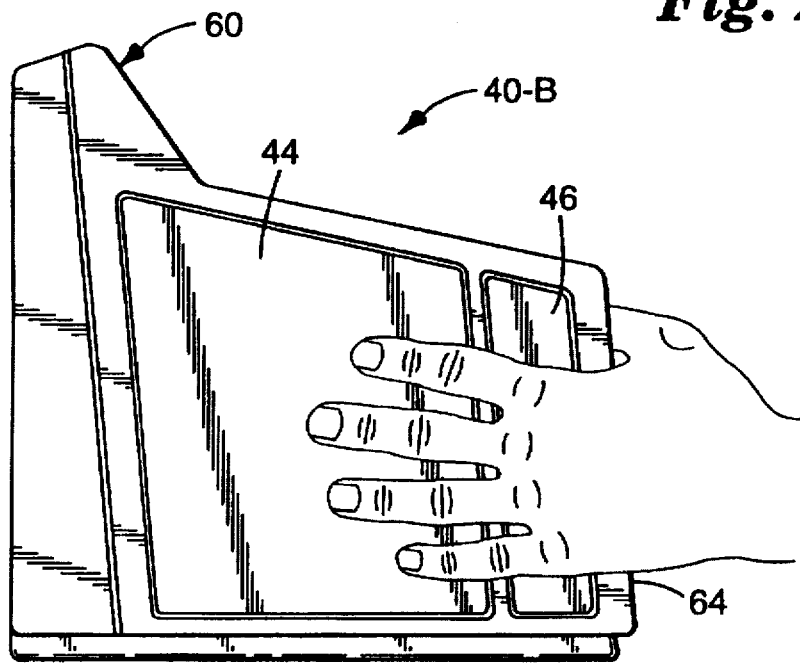

FIG. 2 is a counter-mounted embodiment of the security access instrument, shown in three views, 2a–2c. FIG. 2a shows semi-frontal view 40-A; FIG. 2b shows side plan view 40-B; and FIG.2c shows top plan view 40-C. Counter-mounted security access instrument 60 has a thumb or finger positioning cavity 62 preferably with an indented platten, for receiving the thumb or finger comfortably, open through front surface 64, extending to the interior of the instrument providing access to detector window 42 and other sensor elements described below, wherein the sensors are protected from stray light. The location and configuration of cavity 62 allows positioning of both left and right hand of the individual seeking authentication on biomedical electrodes 44, 46, 48, and 50 with the thumb or finger of one hand properly oriented on detector window 42 inside cavity 62. A switch (not shown) can be mounted on the instrument 60 adjacent electrodes in order to activate scanning.

Detector window 42 can be a prism for redirecting light, preferably having a coating to present a good "feel" to the user while protecting window 42.

This configuration is only one of many that would allow for positioning of the hands or other body parts in contact with the EKG electrodes while also providing positions for a selected finger or toe on the fingerprint scanner. For example, the measurement section could be essentially flat with the detector window in the center and EKG electrodes configured on either side such that a toe or finger could be positioned on the detector window and EKG contact made to parts of the hand or foot.

FIGS. 2a and 2c show a keypad 54 for entry of PIN or other coded information input and display window 56 for information and status output. This configuration can be expanded to include readers for ID cards or memory devices and sound transducers for verbal or sound tone input or output.

This counter-mounted embodiment of the security access instrument is connected by appropriate electrical cables (not shown) to a computer for power, signal and data communication. Further equipment could easily be built into the access instrument to include microprocessor and memory for handling the computer related logic functions, power supply, and output devices; such that the output of this instrument would be a simple call signal for use with a relay or other response apparatus to allow the individual access to the secured equipment or facility after authentication is obtained.

Figure 3A:
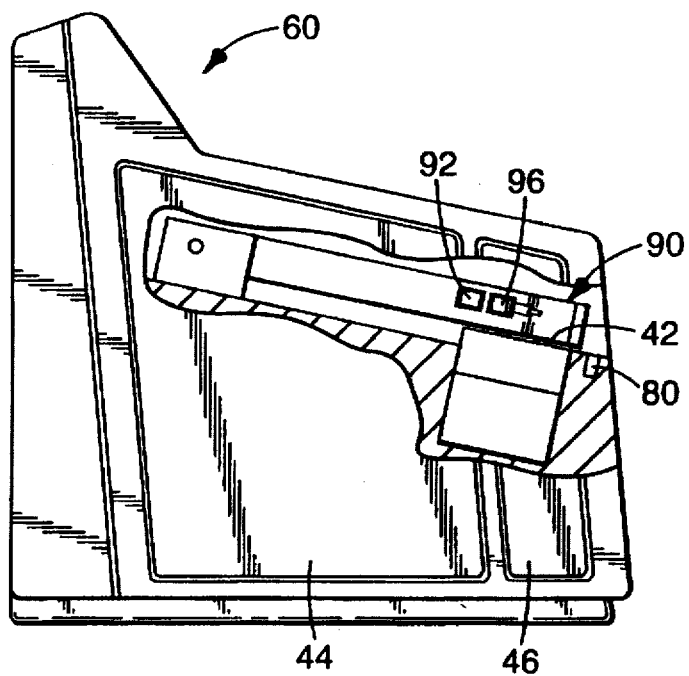
FIGS. 3a, 3b, and 3c are cutaway views of a preferred embodiment of the invention showing positions of the measurement apparatus.
Figure 3B:
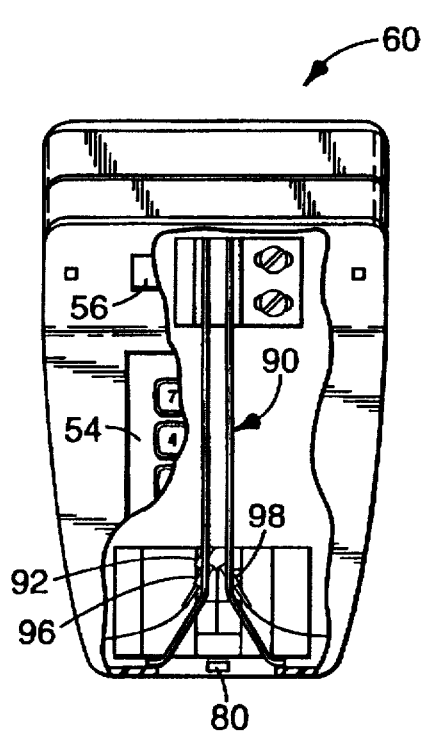
Figure 3C:
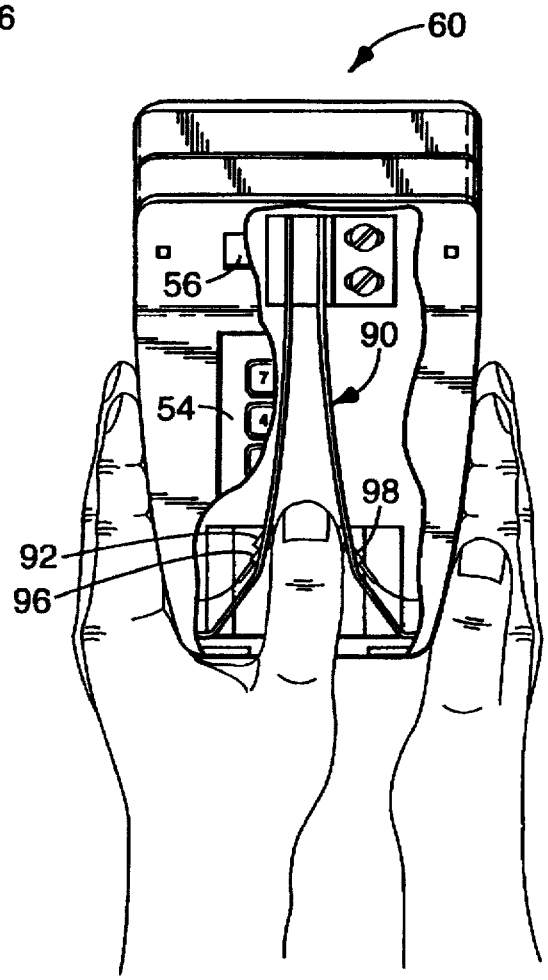

FIGS. 3a–3c show the counter-mounted embodiment of the security access instrument, in partial cutaways detailing the position of window 42 with respect to spring assembly 90 such that light emitting diodes 92 and 96 are essentially diametrically opposite photodetector 98. Alternatively, light emitting diodes 92 and 96 and photodetector 98 can be mounted above and below the thumb positioning cavity. Optional skin temperature sensor 80 is positioned next to window 42 in line with the entry axis of the thumb positioning cavity 62 to be in contact with the skin near connection of the thumbprint region of the hand.

Figure 4:
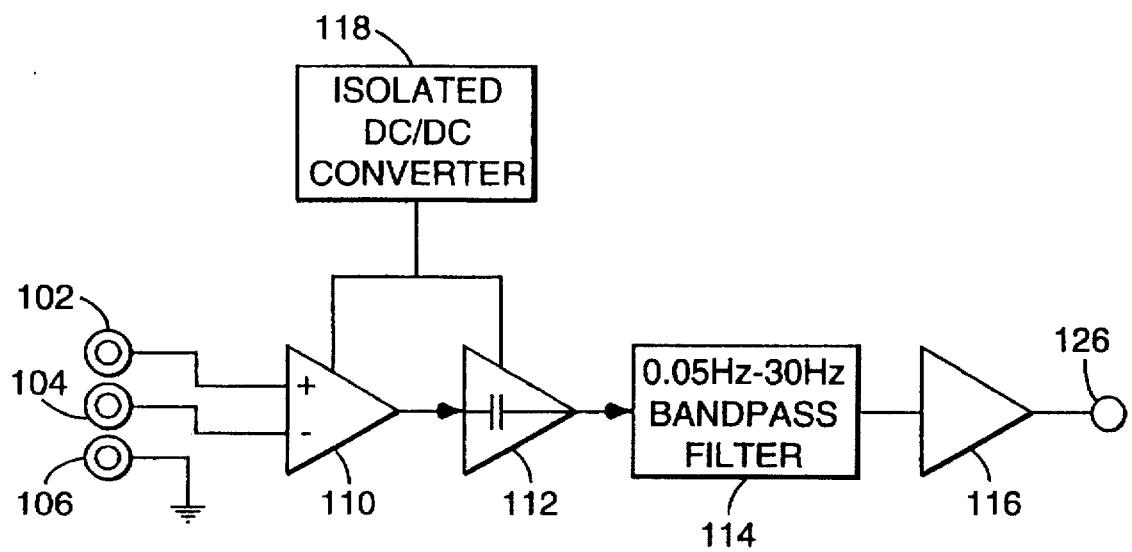
FIG. 4 is a block diagram of the apparatus for recognizing the non-specific biometric parameter of electrocardiographic signals.
Figure 6:
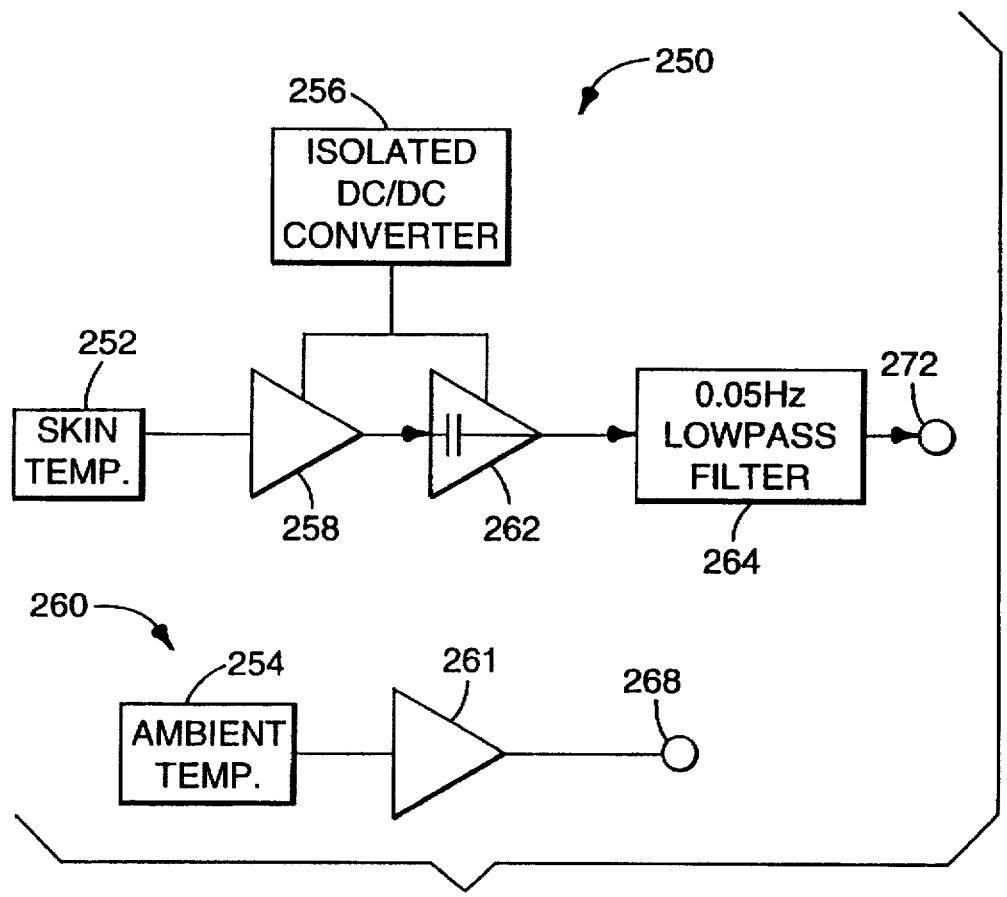
FIG. 6 is a block diagram of the apparatus for recognizing the non-specific biometric parameter of skin temperature.

FIGS. 4, 5, and 6 are block diagrams of circuitry for the devices for measuring the non-specific biometric parameters—EKG, blood oxygen, pulse, and skin temperature.—expanding the content of sensor interface electronics block 30, and sensors 24, 26 and 28.

The sensors 24 used for EKG detection are signal electrodes 102 and 104 plus ground electrode 106 shown in FIG. 4. These are the same electrodes as 46 and 48, and ground electrodes 44 and 50 (which are connected together) of FIG. 2, respectively, wherein ground electrode 106 and first biomedical electrode 104 contact the left hand and second biomedical electrode 102 contacts the right hand (not shown).

Biomedical electrodes useful in the present invention are commercially available from Minnesota Mining and Manufacturing Company, St. Paul, Minn. Particularly preferred are biomedical electrodes described in U.S. Pat. No. 5,012, 810 (Strand et al.); U.S. Pat. Nos. 4,524,087; 4,539,996; 4,554,924; and 4,848,353 (all Engel); and U.S. Pat. No. 5,133,356 (Bryan et al.), the disclosures of which are incorporated by reference.

Electrodes 102, 104, and 106 are mounted with conductive adhesive surfaces exposed for contact with fingers or thumbs. Electrodes 102, 104, and 106 are changed periodically as the conductive adhesive contact surface is contaminated by dirt and dry skin flakes. Electrodes 102 and 104 are connected to the inputs of differential instrumentation amplifier 110 which provides signal amplification with high input impedance as required for efficient interface to electrodes 102 and 104. Instrumentation amplifier 110 is followed by isolation amplifier 112 to provide electrical isolation to the individual. Both instrumentation amplifier 110 and isolation amplifier 112 are powered by isolated DC—DC converter 118 providing safety protection by electrical isolation from the main power supply.

The EKG signal is processed by band pass filter 114 to eliminate unwanted noise outside the 0.05 Hz to 30 Hz frequency band and amplified by buffer amplifier 116 to compensate for signal level from the human body. The processed EKG signal output 126 is communicated to analog to digital interface 22.

A block diagram for blood oxygen saturation sensor is shown in FIG. 5. The sensor is a pulse oximeter type and is well known to those skilled in the art. The emitters and sensors of this device are located in the detector window 42 (shown in FIG. 3), delivering near infrared (NIR) and visible light at multiple wavelengths through human tissue of the thumb and detecting the transmitted light. The light emitters are powered at an alternating rate such that one light is off when the other light is on, the driving rate of the lights is at a frequency much greater than the human heart rate, for example 1500 Hz.

The detected light sampled at the same driving rate and is pulsatile in nature related directly to the normal heart pulse cycle. Change in detected light intensity at the peak and at the valley phases of a particular pulse cycle provides a relative measure of absorbance in the arterial blood. By comparing the relative absorbances at multiple wavelengths (usually about 910 nm and 660 nm), an oxygen saturation value can be determined for the blood of the subject.

Light source 140 delivers light at two wavelengths. One light emitting diode (LED) 142 emitting light at a wavelength of 660 nanometers and one LED 144 emitting light at a wavelength of 910 nanometers are driven by LED drive sources 148 and 150. The LEDs are timed by clock generator 146 generating intermittent on and off condition providing two distinct states for the overall light source: 910 diode on/660 diode off shown as 156, 910 diode off/660 diode on shown as 152.

Detector 170 transduces the transmitted light to an electrical signal with variable current silicon photodiode 172. The variable current signal is converted to a variable voltage by current to voltage amplifier 174. Detection is synchronized with the LED emitter timing, detecting and holding the light level transmitted during each of the two distinct states with sample and hold circuits 182, and 186. Each transmitted light signal includes both a DC and AC components which are separated for the blood oxygen calculation and processing in sensor processor 38. The 910 nanometer signal is amplified 190 and filtered 192 to eliminate unwanted signal above 10 Hz and communicated to interface 22 through connection 198-D. AC component is separated by 0.3 Hz high-pass filter 194, amplified by amplifier 196 and communicated to interface 22 through connection 198-A.

Parallel processing of the 660 nanometer signal is through channel 200, 202, 204, 206 and 208-A and 208-C.

The blood oxygen measurement of this system is well known and described in U.S. Pat. Nos. 4,869,254 and 5,078,136 (Stone et al.), the disclosures of which are incorporated by reference herein. Pulse oximeters are commercially available in the manner described by these patents, including light emitting diodes 142 and 144 and detector 170 sold by Nellcor Incorporated of Hayward, Calif.

Processing of the pulse oximeter signal is described herein as time domain signal processing. Clearly the processing could be done in the frequency domain by digitizing the signal directly at the sensors and using digital signal processing techniques.

Optionally, skin temperature is measured with a solid state sensor chosen for linearity across the temperature range of the human body. Block diagram of the associated measurement circuit 250 is shown in FIG. 6. Skin temperature sensor 252 is supplied by isolated DC/DC converter 256, for protection of the individual. Voltage from sensor 252 is linearly dependent on the temperature, is amplified and isolated from other circuitry by amplifiers 258 and 262. The temperature signal is filtered 264 to eliminate all frequencies above 0.5 Hz. to eliminate electrical noise and communicated to interface 22 through connection 272. Optionally, an ambient temperature sensor 254 may be used to compensate for environmental conditions as shown in block diagram 260. The signal from optional temperature sensor 254 is amplified by amplifier 261 and communicated to interface 22 through connection 268.

Figure 7:
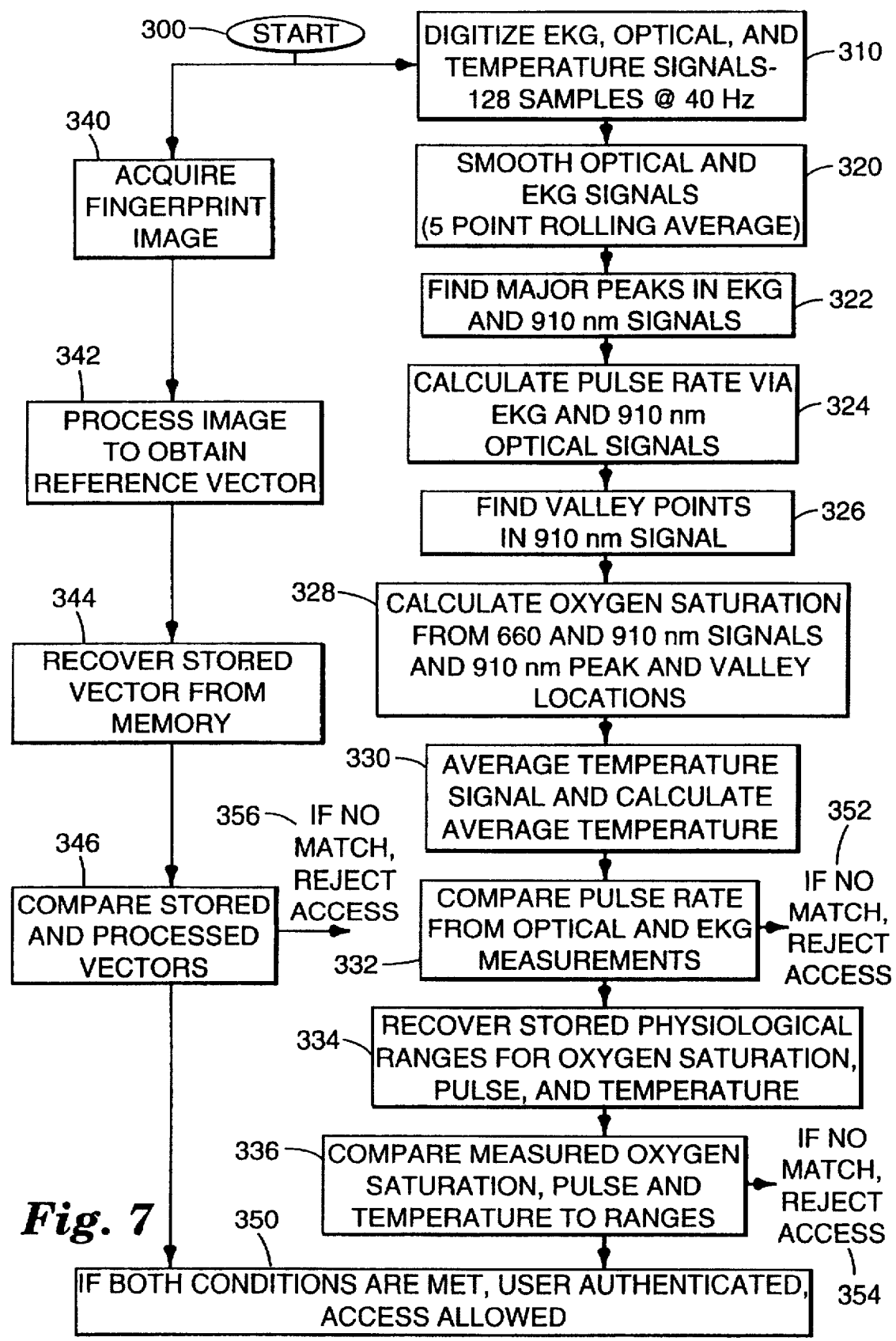
FIG. 7 is a flow chart for completing authentication according to the present invention.

Recognition and comparison for the personal, biometric authentication system is based initially on fingerprint recognition followed by analysis of the biometric sensor signals for: EKG 126, NIR light at 910 nanometer 198-A and 198-C and at 660 nanometer 208-A and 208-C, and temperature 272. Authentication is processed in an embedded logic program within computer 6 using programming written in WATCOM C version 9.5 from WATCOM International Corp, Waterloo, Ontario, Canada computer code in a manner known to those skilled in the art. Description of the recognition subsystems, comparison subsystems, and authentication subsystems is shown in FIG. 7. Alternatively, authentication can be processed using neural network programming in a manner known to those skilled in the art.

Authentication processing as shown in FIG. 7 is started with keying in a PIN by the individual seeking personal authentication or by insertion of an ID card communicating a PIN identification 300. The individual places his or her hands in the locations shown in FIGS. 2a–2c and the individual's fingerprints are scanned 340 and processed to obtain the reference vector 342. The appropriate record 344 is recalled from memory 16 and compared 346 for acceptance or rejection. If the comparison is rejected, authentication has failed, regardless of the comparison arising from the non-specific biometric parameters. In a preferred embodiment, access is denied because of the rejected authentication.

In parallel with the recognition and comparison subsystems used for fingerprint recognition with data from fingerprint storage, the non-specific biometric recognition steps are started concurrently as shown in FIG. 7.

Biometric data are recognized and collected 310 over multiple samples (about 128) of the EKG signal, optical signals, and optional temperature signal taking a period of approximately 3.2 seconds with EKG signal preferably collected in a period of about 0.5 seconds. The logic process then proceeds to analyze the plethysmographic, EKG, and temperature signals by smoothing the optical and EKG signals using a five point rolling average 320, finding the major peaks in the EKG and 910 nm optical signals 322, calculating pulse rate of EKG and optical signals 324, finding valleys in the 910 nm NIR signal 326, calculating the oxygen saturation ratio from 660 nanometer and 910 nanometer optical signals 328, and averaging the temperature signal and calculating the average actual skin temperature 330.

Next a comparison 332 is made of the pulse rate obtained concurrently by the 910 nm optical plethysmography signal and the EKG signals. If the pulse rate as measured by both methods is within an acceptable synchronicity, then logic processing continues. If there is no acceptable synchronicity, then the authentication is rejected 352, regardless of the results of the comparison 346 of fingerprint identification.

If the two pulse rates are within acceptable synchronicity, then physiological norms of oxygen saturation, pulse, and temperature are recalled 334 for comparison 336 with the calculated oxygen saturation ratio 328, the pulse rate 324, and the temperature 310. If there is acceptable comparison 336, then with an acceptable fingerprint comparison 346, there is authentication 350. If there is no acceptable comparison 336, then authentication is rejected 354 regardless of the results of fingerprint comparison 346. As presently preferred, authentication subsystem then grants access to equipment or facilities.

Figure 8:
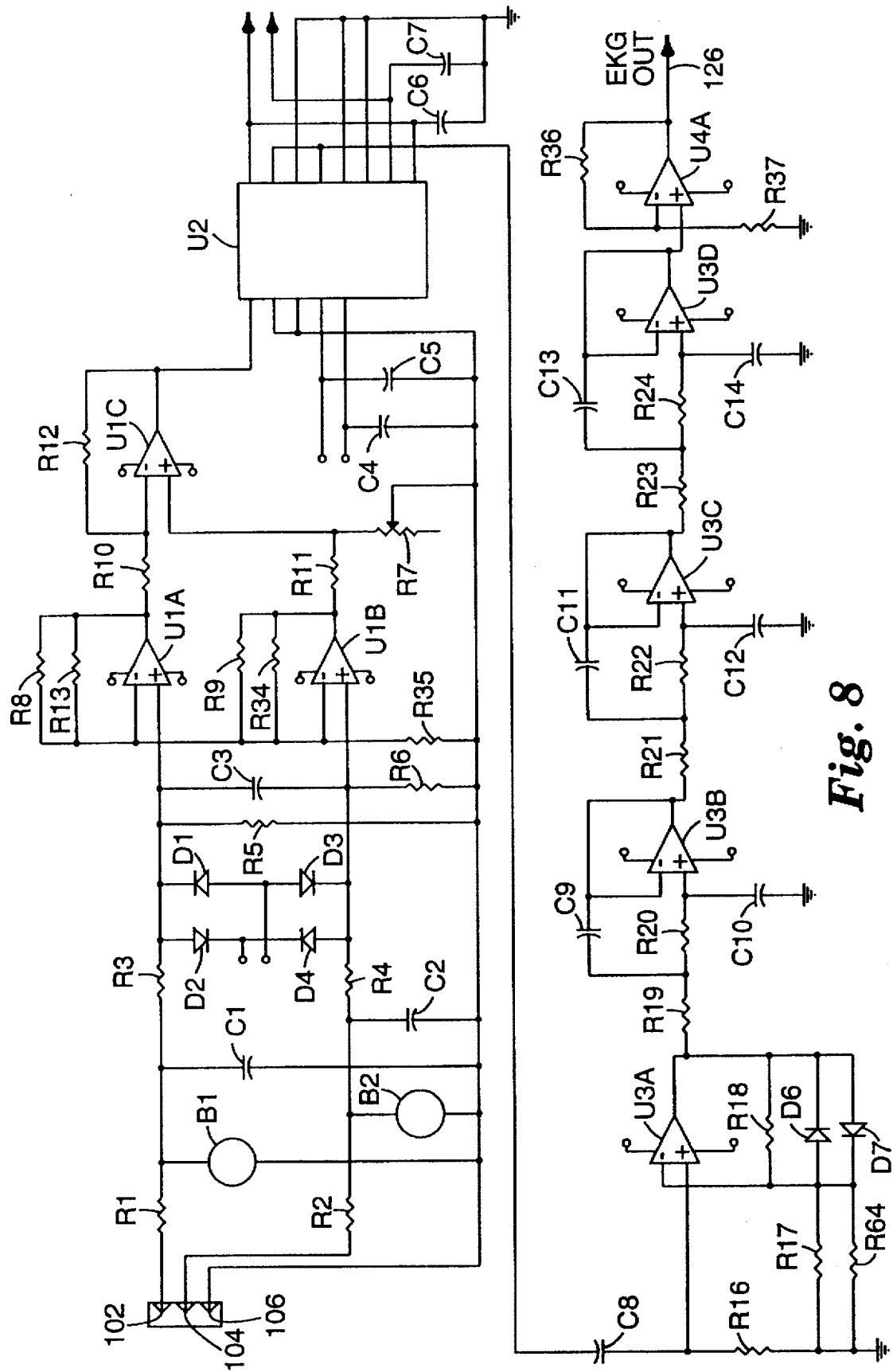
FIG. 8 is an electrical schematic illustration of circuitry for processing the non-specific biometric parameter of electrocardiographic signals as shown in FIG. 4.

FIG. 8 is the detail circuit diagram of the EKG circuit shown as a block diagram in FIG. 4. TABLE 1. is the listing of components and devices used in this circuit.

TABLE 1

| COMPONENTS | |
| --- | --- |
| B1,B2 | NE2H Lamp |
| C1,C2 | 500 pf |
| C3 | 200 pf |
| C4,C5,C8 | 1 µf |
| C6,C7 | 10 µf |
| C9,C10,C11,C12,C13,C14 | 0.56 µf |
| R2,R1 | 300K |
| R3,R4,R7 | 50K |
| R5,R6 | 5M |
| R8,R9,R10,R11,R12 | 20K |
| R13,R34 | 2.2K |
| R14 | 30K |

TABLE 1-continued

| | |
|---|---|
| R16 | 1M |
| R17 | 4.75K |
| R18 | 47K |
| R19,R20,R21,R22,R23,R24 | 10K |
| R35 | 100 |
| R36,R37 | 22K |
| R64 | 1K |
| DEVICES | |
| U1,U3,U4 | LF444CN |
| Operation Amplifier: | |
| National Semiconductor | |
| Santa Clara, CA | |
| U2 | ISO107A |
| High Voltage Isolation Amplifier | |
| Burr-Brown | |
| Tucson, AZ | |
| D1,D2,D3,D4 | 1N4148 |
| D6,D7 | 1N914 |
| Diode: National Semiconductor | |
| Santa Clara, CA | |

Figure 9:
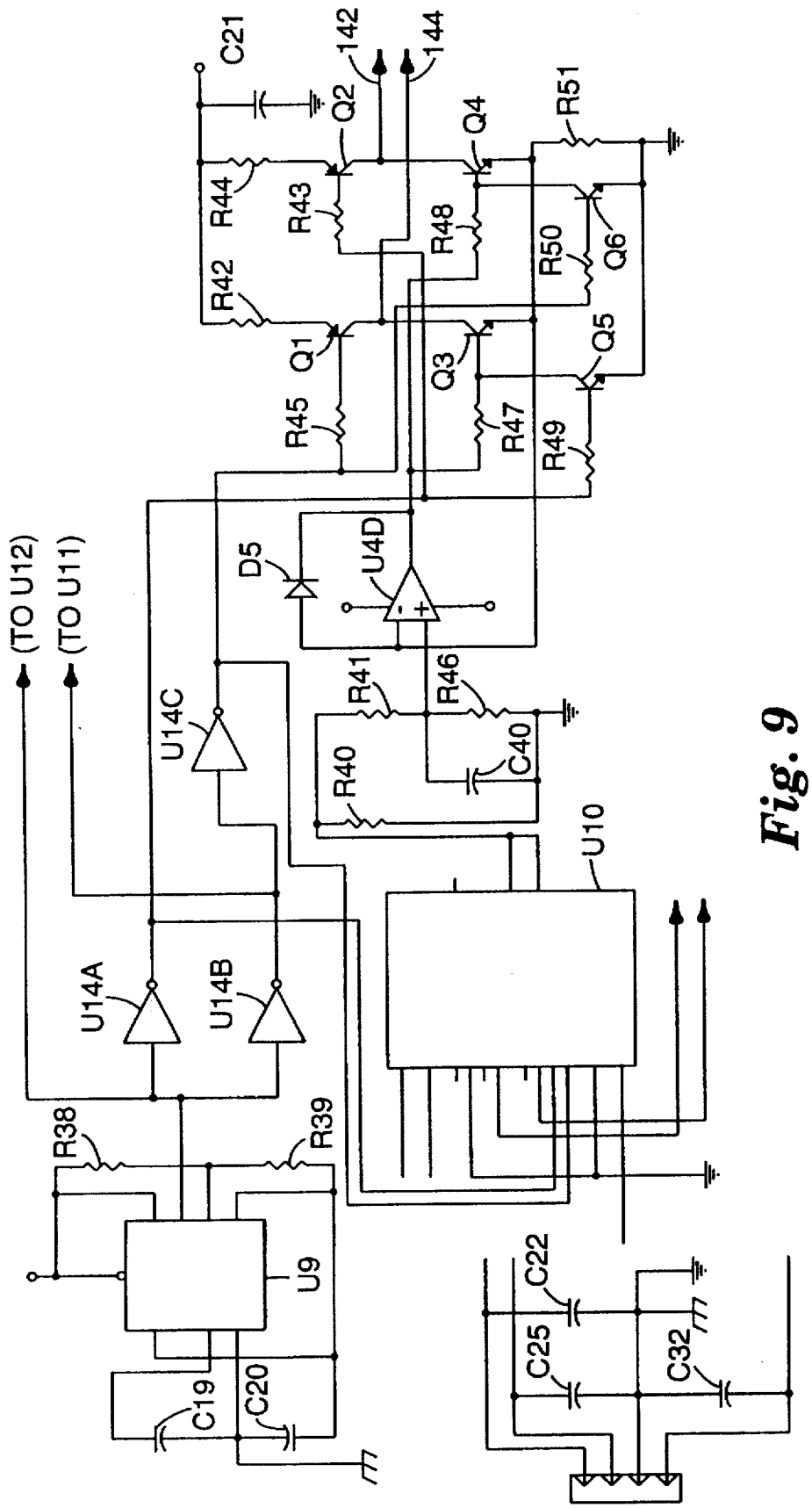
FIG. 9 is an electrical schematic illustration of circuitry for producing pulsating power to the red and IR lamps for the non-specific biometric parameter of blood oxygen saturation as shown in FIG. 5.

FIG. 9 is the detail circuit diagram of the blood oximeter light power circuit shown as a block diagram 140 in FIG. 5. TABLE 2 is the listing of components and devices used in this circuit.

TABLE 2

| COMPONENTS | |
|---|---|
| C21 | 1.0 µf |
| C19 | 0.01 µf |
| C20 | 4700 pf |
| C22 | 4.9 µf |
| C25 | 5.3 µf |
| C32 | 5.4 µf |
| C40 | 1 µf |
| R40 | 1M |
| R41 | 47K |
| R46,R49,R50 | 10K |
| R38 | 1K |
| R39 | 200K |
| R45,R43 | 4.7K |
| R47,R48 | 470Ω |
| R42,R44,R51 | 10Ω |
| DEVICES | |
| U9 | LM555CN - 1500 Hz |
| Clock/Timer: National Semiconductor | |
| Santa Clara, CA | |
| U10 | DG211 |
| Analog Switch: Siliconix | |
| Santa Clara, CA | |
| D5 | 1N4148 |
| Diode: National Semiconductor | |
| Santa Clara, CA | |
| Q1,Q2 | 2N4403 |
| Q3,Q4,Q5,Q6 | 2N4401 |
| Transistor: National Semiconductor | |
| Santa Clara, CA | |
| U4 | LF444C4 |
| Operational Amplifier | |
| National Semiconductor | |
| Santa Clara, CA | |
| U14 | 74HCT04 |
| Gate | |
| National Semiconductor | |
| Santa Clara, CA | |

Figure 10:
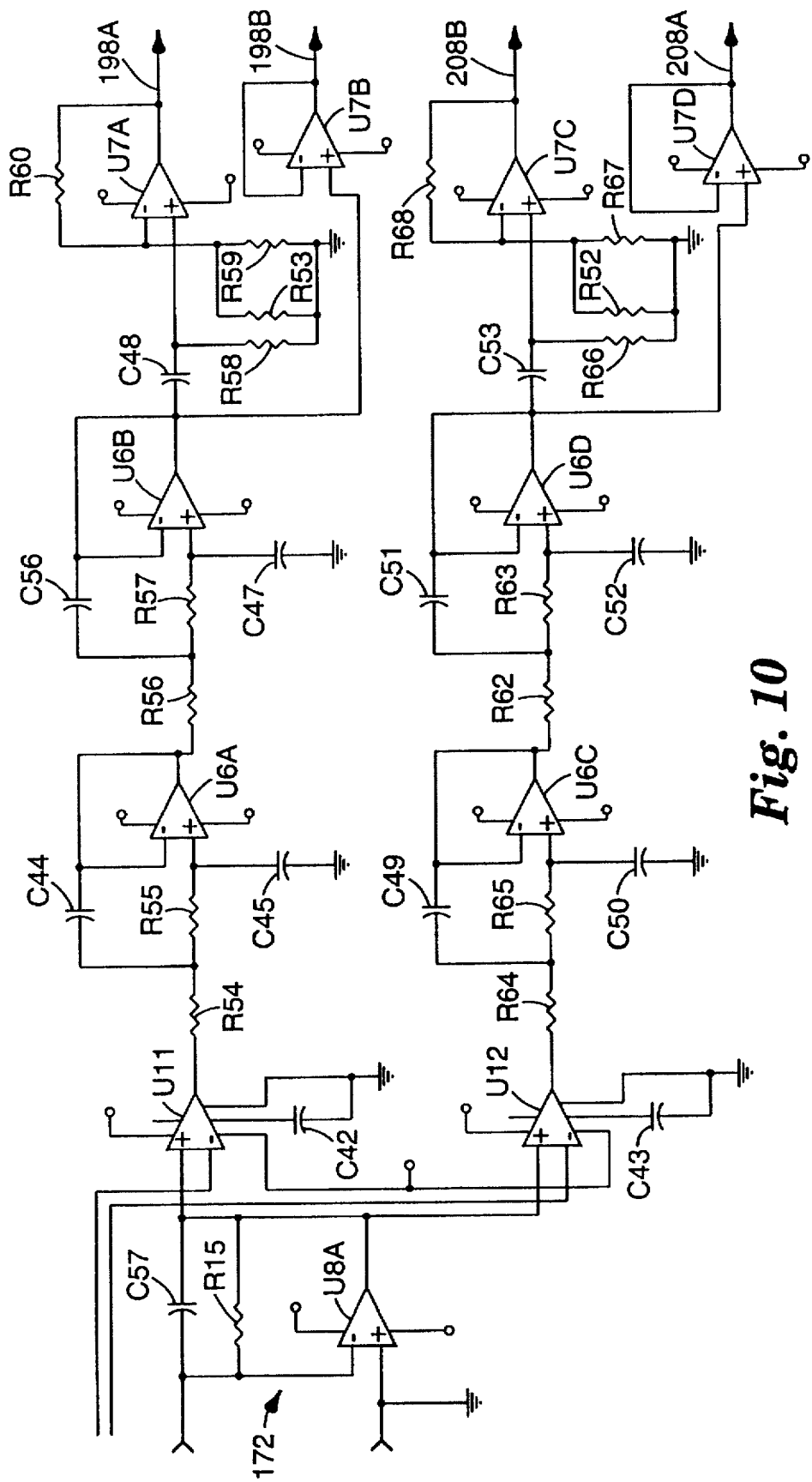
FIG. 10 is an electrical schematic illustration of circuitry for processing the signals indicating non-specific biometric parameter of blood oxygen saturation as shown in FIG. 5.

FIG. 10 is the detail circuit diagram of the blood oximeter read circuit shown as a block diagram 170 in FIG. 5. TABLE 3 is the listing of components and devices used in this circuit.

TABLE 3

| COMPONENTS | |
|---|---|
| C42,C43 | 0.1 µf |
| C44,C45,C47,C48,C49, C50,C52,C53,C56 | 0.47 µf |
| C57 | 10 pf |
| R15 | 10M |
| R54,R55,R56,R57, R62,R63,R64,R65 | 25K |
| R52,R53 | 560 |
| R66,R58 | 1.0M |
| R67,R59 | 5K |
| R60,R68 | 330K |
| DEVICES | |
| U6,U8,U8 | LF444CN |
| Operation Amplifier: | |
| National Semiconductor, Santa Clara, CA | |
| U12,U11 | LF398 |
| Sample and Hold: | |
| National Semiconductor, Santa Clara, CA | |

Figure 11:
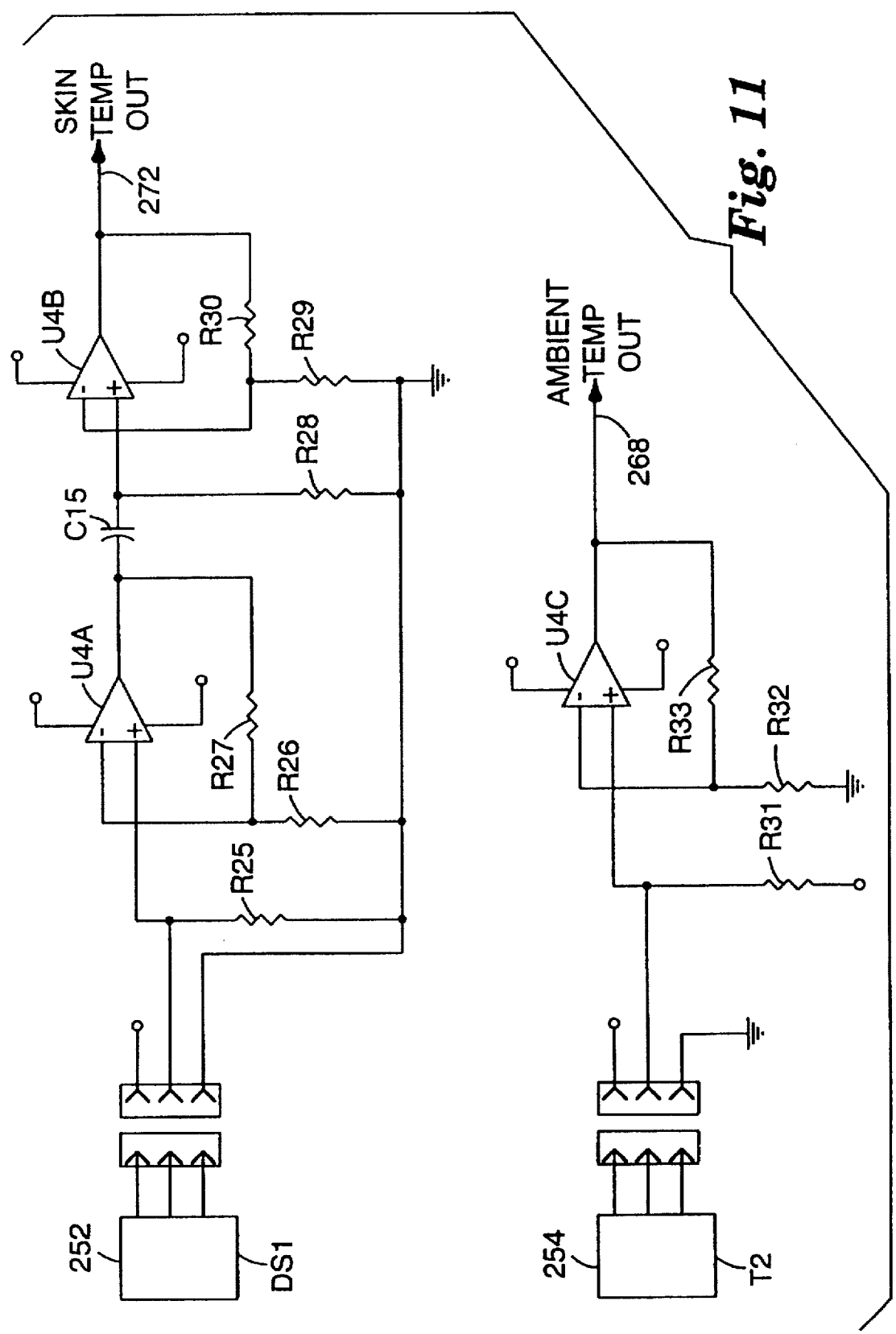
FIG. 11 is an electrical schematic illustration of circuitry for the temperature sensor circuit shown as a block diagram in FIG. 6.

FIG. 11 is the detail circuit diagram of the temperature sensor circuit shown as block diagrams 250 and 260 in FIG. 6. TABLE 4 is the listing of components and devices used in this circuit.

TABLE 4

| COMPONENTS | |
|---|---|
| C15 | 1.0 µf |
| R30 | 475K |
| R26,R29,R32,R33 | 4.75K |
| R28,R25 | 100K |
| R27 | 23.5K |
| R31 | 240K |
| DEVICES | |
| U4 | LF444CN |
| Operation Amplifier: | |
| National Semiconductor | |
| Santa Clara, CA | |
| DS1 | E10051 |
| Murata Manufacturing Co. Ltd. | |
| Kyoto, Japan | |
| T2 | LM34 |
| National Semiconductor | |
| Santa Clara, CA | |

While embodiments of the invention have been disclosed, the following claims disclose the scope of the invention.

What is claimed is:

1. A biometric, personal authentication system, comprising:

(a) storage subsystem to store a unique, inherently specific biometric parameter from at least one individual in a species;

(b) first detection subsystem to detect the unique, inherently specific biometric parameter in an individual seeking personal authentication;

(c) second detection subsystem to detect at least one non-specific biometric parameter of a physiological characteristic having measurable variability during the time of authentication in the individual seeking personal authentication, wherein the non-specific biometric parameter is selected from the group consisting of pulse rate, electrocardiographic signals, spectral characteristics of human tissue, percentage oxygenation of blood, bloodflow, hematocrit, biochemical assays of tissue, electrical plethysmography, transpiration of gases, electrical property of skin, blood pressure, differential blood volumes, and combinations thereof;

(d) first comparison subsystem to compare the unique, inherently specific biometric parameter detected by the first detection subsystem with the unique, inherently specific biometric parameter stored in the storage subsystem;

(e) second comparison subsystem to compare each non-specific biometric parameter to physiological norms for the species; and (f) authentication subsystem to confirm identity of the individual seeking personal authentication by evaluating the comparisons made by first comparison subsystem and second comparison subsystem.

2. The system according to claim 1, wherein second detection subsystem detects and second comparison subsystem compares at least two non-specific biometric parameters with a physiological correlation between the two non-specific biometric parameters within an acceptable range.

3. The system according to claim 1, wherein storage subsystem is used to limit database searching by processing a personal identification code number.

4. The system according to claim 1, wherein storage subsystem is resident on a card possessed by an individual.

5. The system according to claim 1, wherein the storage subsystem also enrolls data of the unique, inherently biometric detection system.

6. The system according to claim 1, wherein the non-specific biometric parameters further include skin temperature.

7. The system according to claim 1, wherein the unique, inherently specific biometric parameter is selected from the group consisting of fingerprint, palm print, voice print, and retinal configuration.

8. The system according to claim 1, wherein the unique inherently specific biometric parameter comprises a pore print.

9. The system according to claim 6, wherein the unique, inherently specific biometric parameter is selected from the group consisting of fingerprint, palm print, voice print, and retinal configuration.

10. The system according to claim 6, wherein the unique, inherently specific biometric parameter comprises a pore print.

11. The system according to claim 9, further comprising an access subsystem to measure alcohol or controlled chemical substance levels in blood of an individual successfully authenticated.

12. A method to authenticate an individual comprising the steps of:

(a) placing both hands of an individual in a device containing a personal authentication system that concurrently detects a unique, inherently specific biometric parameter and detects at least one non-specific biometric parameter of a physiological characteristic having measurable variability during the time of authentication; wherein the non-specific biometric parameter is selected from the group consisting of pulse rate, electrocardiographic signals, spectral characteristics of human tissue, percentage oxygenation of blood, bloodflow, hematocrit, biochemical assays of tissue, electrical plethysmography, transpiration of gases, electrical property of skin, blood pressure, differential blood volumes, and combinations thereof; and (b) comparing biometric parameters detected by the system to confirm identity of the individual seeking personal authentication.

13. A biometric, personal authentication system for controlling access to a facility by determining authentication of an individual seeking access to the facility, comprising:

(a) storage subsystem to store a unique, inherently specific biometric parameter from at least one individual in a species;

(b) first detection subsystem to detect the unique, inherently specific biometric parameter in an individual seeking personal authentication;

(c) second detection subsystem to detect at least one non-specific biometric parameter of a physiological characteristic having measurable variability during the time of authentication in the individual seeking personal authentication; wherein the non-specific biometric parameter is selected from the group consisting of pulse rate, electrocardiographic signals, spectral characteristics of human tissue, percentage oxygenation of blood, bloodflow, hematocrit, biochemical assays of tissue, electrical plethysmography, transpiration of gases, electrical property of skin, blood pressure, differential blood volumes, and combinations thereof;

(d) first comparison subsystem to compare the unique, inherently specific biometric parameter detected by the first detection subsystem with the unique, inherently specific biometric parameter stored in the storage subsystem;

(e) second comparison subsystem to compare each non-specific biometric parameter to physiological norms for the species; and (f) authentication subsystem to confirm identity of the individual seeking personal authentication by evaluating the comparisons made by first comparison subsystem and second comparison subsystem, wherein the system further comprises an access subsystem to measure alcohol or controlled chemical substance levels in blood of an individual successfully authenticated and wherein access to the equipment is controlled by the access subsystem after an individual is successfully authenticated; and wherein the second detection subsystem detects and the second comparison subsystem compares at least two non-specific biometric parameters with a physiological correlation between the two non-specific biometric parameters within an acceptable range.

\* \* \* \* \*